United States Patent [19]

Fujisawa et al.

[11] Patent Number: 4,931,096
[45] Date of Patent: Jun. 5, 1990

[54] SEALER FOR FILLING A DENTAL ROOT CANAL

[75] Inventors: Mutsuo Fujisawa, Musashino; Tsutomu Kameda; Hirofumi Katsura, both of Morioka; Reiichi Yamaga, Takatsuki; Setsuko Ishido, Kiyose, all of Japan

[73] Assignee: Toyo Chemical Laboratories, Inc., Tokyo, Japan

[21] Appl. No.: 246,693

[22] Filed: Sep. 20, 1988

[30] Foreign Application Priority Data

Feb. 9, 1988 [JP] Japan ................................. 63-26704
Jul. 7, 1988 [JP] Japan ................................. 63-167715

[51] Int. Cl.$^5$ .................................................. A61K 6/08
[52] U.S. Cl. ........................................ 106/35; 433/224; 433/226; 433/228.1; 523/113; 523/115; 523/118; 524/575.5; 524/925; 524/928; 524/929
[58] Field of Search ............... 106/35; 524/575.5, 925, 524/928, 929; 433/224, 226, 228.1; 523/113, 115, 118

[56] References Cited

U.S. PATENT DOCUMENTS

| | | | |
|---|---|---|---|
| 2,077,396 | 4/1937 | Charch et al. | 106/230 |
| 3,883,459 | 5/1975 | Kent | 264/230 |
| 4,184,879 | 1/1980 | Ducos et al. | 106/35 |
| 4,483,679 | 11/1984 | Fujisawa et al. | 106/35 |
| 4,647,600 | 3/1987 | Kawahara et al. | 106/35 |
| 4,740,245 | 4/1988 | Futami et al. | 106/35 |

FOREIGN PATENT DOCUMENTS 53-036995 4/1978 Japan .

OTHER PUBLICATIONS

Conrad, W. K., "Materials Used in Root-Canal Technique in Dental Practice", *Dental Cosmos*, vol. LXXVI, Mar. 1934, pp. 311-315.
Skinner et al., *The Science of Dental Materials*, pub. W. B. Saunders Co., Philadelphia, 1967, p. 514.

*Primary Examiner*—Paul Lieberman
*Assistant Examiner*—Linda D. Skaling
*Attorney, Agent, or Firm*—Fleit, Jacobson, Cohn, Price, Holman & Stern

[57] ABSTRACT

A sealer for filling a dental root canal which can seal the apex of the root and the root canal perfectly and can be removed with the gutta percha points when refilling is necessary.

The sealer of the invention consists of the same basic material as the gutta percha point, so it adheres to the point initimately and firmly and can seal the apex of the root perfectly. The softening temperature of the sealer is about 40°-45° C., so the points and the sealer can be removed same time by heating at low temperature with a heat carrier when refilling is necessary.

3 Claims, No Drawings

SEALER FOR FILLING A DENTAL ROOT CANAL

BACKGROUND OF THE INVENTION (1) Field of the Invention

The invention relates to a sealer for filling a dental root canal, more particularly, it relates to a sealer for filling a dental canal based on gutta percha, or polyisoprene, or a mixture thereof.

(2) Description of the Prior Art

The method of root canal filling in dental treatment (Endodontics) is the extirpation of the tooth pulp in the first place and after enlargement and disinfection of the root canal, it is completely sealed with gutta percha points by either lateral condensation or vertical condensation. The object of the method is to intercept the infection by bacteria from an orifice of the root canal and to preserve teeth.

It is difficult, however, to seal completely the inside root canal with the gutta percha points, so a paste of calcium hydroxide or eugenol cement system is stuck to a main gutta percha point as a sealer to accomplish complete sealing of an apex of the root. But, pH and the quality of the paste gives a patient a passing stimulus, so treatment of a lesion of the apex of the root is often retarded.

Furthermore, a perfect seal is only confirmed by X-ray after the root canal filling and in the case of the filling being is imperfect accidentally, it is necessary to remove completely the materials filled in the root canal for refilling.

But, it is impossible to remove the materials completely because the paste of calcium hydroxide and eugenol cement system used has hardened to being infusible. For this reason, it often occurs that a tooth must be extracted.

SUMMARY OF THE INVENTION

It is an object of the present invention to provide a sealer which can perfectly seal the apex of the root and can be removed by heating or using a small quantity of chloroform when resealing is necessary.

This and other objects have been attained by the sealer which consists of the same basic materials as a gutta percha point which has been used to fill the dental root canal.

Namely, the invention comprises gutta percha, or polyisoprene machine thereof, as well as zinc oxide, liquid paraffin, Japan wax and a radio-opaque material.

The conventional sealer hardens by chemical reaction and cannot be removed by heating, physically or using chemical agents when a refilling is necessary because of an imperfect filling and has as a worst result, the extraction of a tooth.

This invention is intented to solve the above-mentioned problems.

DESCRIPTION OF THE PREFERRED EMBODIMENT

This invention is a sealer for filling a dental root canal comprising gutta percha, or polyisoprene, or mixtures thereof, as well as zinc oxide, liquid paraffin, Japan wax and a radio-opaque material. Hereinafter, quantities are expressed as % by weight.

The content of gutta percha, or polyisoprene, or a mixture thereof is preferably 3-20%. The fluidity of the sealer decreases above 20% and sealing of the apex of the root becomes imperfect and the strength of sealer hardened decreases under 3%. Zinc oxide acts as cement to seal the apex of the root and its content is preferably 30-70%. The toughness decreases above 70% and sealing power decreases under 30%. Liquid paraffin gives fluidity and softness by heat to the sealer and its content is preferably 3-15%. The strength of the sealer decreases above 15% and the fluidity decreases under 3%. Japan wax is concerned in the operation of filling and its content preferably is 2-26%. It is too soft to press the sealer above 26% and hardening is too fast to press it under 2%. A radio-opaque material is used for the confirmation of perfect filling after the operation of the root canal filling. Barium sulfate or iodoform is contained as the radio-opaque material and its effective content is 2-30%.

The sealer may contain some amount of a pigment from esthetic point of view because it is white and its proper quantity is 0.5-2.0%.

The perfect sealing of the apex of the root is confirmed in the experiment by sticking the sealer set forth above on the main gutta percha point and the gutta percha point is removed with the sealer by inserting a heat carrier slightly heated in the apex of the root in the case of imperfect sealing.

Furthermore, the experiment relates to the sealing ability of the root canal which is one of the most important physical properties which is performed by the method of dye permeation.

The sealer of the present invention has a smaller degree of the dye permeation than conventional sealer of calcium hydroxide and zinc oxide-eugenol cement system and this fact shows the prominent sealing ability of the present invention.

The following examples are included merely to aid in the understanding of the invention, and variations may be made by one skilled in the art without departing from the spirit and scope of the invention.

EXAMPLE 1

Gutta percha: 14%
Zinc oxide: 50%
Liquid paraffin: 6%
Japan wax: 4%
Barium sulfate: 26%

The softness (Paste state) retaining time was about 2 minutes at 37° C. and the hardening was sharp.

EXAMPLE 2

Gutta percha: 12%
Zinc oxide: 30%
Liquid paraffin: 20%
Japan wax: 20%
Iodoform: 18%

The softness (Paste state) retaining time was about 4 minutes at 37° C., so the operation time to fill was sufficient.

EXAMPLE 3

Polyisoprene: 14%
Zinc oxide: 55%
Liquid paraffin: 7%
Japan Wax: 9%
Barium sulfate: 15%

The softness (Paste state) retaining time was about 2 minutes at 37° C. and it appeared that the operation time to fill was somewhat short.

EXAMPLE 4

Polyisoprene: 15%
Zinc oxide: 60%
Liquid paraffin: 10%
Japan wax: 10%
Iodoform: 5%

The softness (Paste state) retaining time was about 2 minutes at 37° C. and it appeared that the operation time to fill was somewhat short.

The comparison of the sealing ability of the root canal by the dye permeation.

EXPERIMENT 1

(1) The dye solution: Red color No. 213 of the legal dye (Rodamine B)0.6% aqueous solution.
(2) The sample was made by the method which the maker designated and it was filled in the glass tube of 1.5 mm inside diameter and 15 mm length and then one side of the tube was sealed with zinc phosphate cement. 12 samples were made for every kind of sealer.
(3) The samples filled with several kinds of the sealer were immersed wholly in the dye solution at the temperature of 37°±0.2° C. immediately after they were filled. The lengths permeated in the samples by the dye solution were measured on 1,3 and 7 days after immersion. Results of permeation test are listed in Table 1.

TABLE 1

| | Unit(mm) ( ) indicates S.D. | | |
| --- | --- | --- | --- |
| | 1 day | 2 days | 7 days |
| Foreign production A | 1.8(0.3) | 2.0(0.5) | 2.0(0.5) |
| Foreign production B | 4.3(1.5) | 15(0) | 15(0) |
| Home product A | 3.6(1.2) | 8.0(2.4) | 15(0) |
| Sealer of the present invention | 1.2(0.2) | 1.8(0.5) | 1.8(0.5) |

EXPERIMENT 2

(1) Several kinds of sealers were filled in root canals of extracted teeth (Anterior teeth) formed by the usual method. 5 samples were made for every kind of sealer.
(2) The orifice of root canal of every tooth was sealed with the cement after the sealer was filled as Experiment 1 and the surface of the tooth was covered with the enamel of manicure except the apex of the root.
(3) The samples were immersed wholly in the dye solution described in Experiment 1.
(4) Every tooth was cut in half on 7 days after the immersion and the length permeated by the dye solution from the apex of the root was measured. Results of the permeation test are listed in Table 2.

TABLE 2

| | Unit(mm) ( ) indicates S.D. 7 days |
| --- | --- |
| Foreign production A | 2.6(0.92) |
| Foreign production B | 7.0(1.5) |
| Home product A | 3.7(0.96) |
| Sealer of the invention | 1.9(0.06) |

The degree of dye solution permeation of the sealer of the invention is small and it is proved that the sealing ability is excellent.

The sealer which consists of above-mentioned components was heated and attached to the main gutta percha point and inserted into the apex of the root. Then, accessory points were filled by the ordinary method and the sealing of the apex of the root and the root canal was perfect.

The gutta percha points and the sealer were removed at the same time by a heat carrier heated about 40° C.

The sealer of the invention contains gutta percha, or polyisoprene, or a mixture thereof, which is the same basic material as a gutta percha point, it adheres to the point intimately and firmly and can seal the apex of the root perfectly. Furthermore, the softening temperature of the sealer is 40°-45° C., so the point and the sealer can be removed at the same time by heating at low temperature when a refilling of the root canal is necessary.

Preferred embodiments of the present invention have been set forth above for the purpose of explaining the invention. It is to be understood, however, that variations and changes may be made in such preferred embodiments, which are nevertheless within the scope and spirit of the invention, as set forth in the following claims.

We claim:

1. A dental root canal filling material comprising a gutta percha point and a sealer composition carried by said gutta percha point, said sealer composition comprising 3 to 20% by weight of gutta percha, or polyisoprene or a mixture thereof, 30 to 70% by weight of zinc oxide, 3 to 15% by weight of liquid paraffin, 2 to 26% by weight of Japan wax and 2 to 50% by weight of a radio-opaque material.

2. A dental root canal filling material as in claim 1, wherein the radio-opaque material is barium sulfate.

3. A dental root canal filing material as in claim 1, wherein the radio-opaque material is iodoform.

* * * * *

UNITED STATES PATENT AND TRADEMARK OFFICE
CERTIFICATE OF CORRECTION

PATENT NO. : 4,931,096

DATED : June 5, 1990

INVENTOR(S) : Mutsuo Fujisawa, Tsutomu Kameda, Hirofumi Katsura, Reiichi Yamaga, Setsuko Ishido It is certified that error appears in the above-identified patent and that said Letters Patent is hereby corrected as shown below:

Col. 1, line 48, cancel "machine", insert --mixtures--.

Col. 4, line 47, cancel "50%", insert --30%--.

Signed and Sealed this

Twenty-fifth Day of June, 1991

Attest:

Attesting Officer

HARRY F. MANBECK, JR.

Commissioner of Patents and Trademarks